(12) United States Patent
Del Zio et al.

(10) Patent No.: US 8,899,096 B2
(45) Date of Patent: Dec. 2, 2014

(54) HIGH-THROUGHPUT MODULAR HYDROGEN STORAGE ENGINEERING PROPERTIES ANALYZER

(75) Inventors: Michael Robert Del Zio, Ann Arbor, MI (US); Jun Yang, Ann Arbor, MI (US); Andrea Pulskamp, Plymouth, MI (US); Shinichi Hirano, West Bloomfield, MI (US); Donald J. Siegel, Ann Arbor, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 336 days.

(21) Appl. No.: 13/404,093

(22) Filed: Feb. 24, 2012

(65) Prior Publication Data

US 2013/0219993 A1  Aug. 29, 2013

(51) Int. Cl.
  *G01N 25/00* (2006.01)
  *B65B 3/00* (2006.01)

(52) U.S. Cl.
  USPC .............................................. 73/25.01; 206/6

(58) Field of Classification Search
  CPC  Y02E 60/321; F17C 11/005; F17C 2221/012
  USPC .................................... 73/25.01; 206/0.6, 0.7
  See application file for complete search history.

(56) References Cited

U.S. PATENT DOCUMENTS

| | | | |
|---|---|---|---|
| 4,436,537 A | 3/1984 | Turillon | |
| 4,609,038 A | 9/1986 | Ishikawa et al. | |
| 4,673,651 A * | 6/1987 | Rothenberg et al. | 435/305.2 |
| 4,819,718 A | 4/1989 | Ishikawa et al. | |
| 6,267,229 B1 | 7/2001 | Heung | |
| 6,478,077 B1 | 11/2002 | Story et al. | |
| 7,721,601 B2 | 5/2010 | Yen et al. | |
| 2004/0149160 A1* | 8/2004 | Foesel et al. | 105/35 |
| 2005/0282755 A1* | 12/2005 | Hart et al. | 514/14 |
| 2008/0215259 A1* | 9/2008 | Hairston | 702/47 |
| 2009/0020429 A1* | 1/2009 | Ozawa et al. | 204/604 |
| 2009/0185972 A1 | 7/2009 | Lee et al. | |
| 2009/0220984 A1* | 9/2009 | Dinges | 435/6 |
| 2010/0115970 A1 | 5/2010 | Lee et al. | |

* cited by examiner

*Primary Examiner* — Hezron E Williams
*Assistant Examiner* — David Z Huang
(74) *Attorney, Agent, or Firm* — Damian Porcari; Brooks Kushman P.C.

(57) ABSTRACT

A cover, sample tray and base may form a hydrogen storage engineering properties analyzer. In at least one embodiment, the sample tray includes a plurality of cooling fins, each of which includes a sample well therein. A variety of hydrogen storage materials may be loaded into and unloaded from each sample well by way of a respective sample well opening. The combined cover and sample tray define at least one plenum which may be in fluid communication between a source of pressurized hydrogen gas and each sample well. The cooling fins may be received by a cooling chamber defined within the base and configured to receive a through-flow of heat-exchange fluid. Certain embodiments may include one or more pressure transducers in fluid communication between the plenum and hydrogen source, and thermal transducers connected to portions of the cooling fins.

16 Claims, 5 Drawing Sheets

HIGH-THROUGHPUT MODULAR HYDROGEN STORAGE ENGINEERING PROPERTIES ANALYZER

TECHNICAL FIELD

The present disclosure relates to a device for facilitating the evaluation of thermal and storage properties of a wide variety of hydrogen storage materials, including the analysis of interfacial thermal interaction between those hydrogen storage materials and various heat exchanging materials.

BACKGROUND

Hydrogen storage materials show considerable benefits in volumetric efficiency over simple pressurized storage tanks These materials typically span a wide range of required operating pressure-temperature conditions which are necessary to achieve their maximum hydrogen storage capacity. For example, sorbents typically call for storage at cryogenic temperatures (e.g., 77 K) whereas complex and chemical hydrides rely on heating (to as high as 600 K) to facilitate hydrogen release. The U.S. Department of Energy set a 2010 goal to achieve an approximate 3-minute refuel time for these hydrogen storage materials, in an effort to match conventional gasoline tank fill times. On the other hand, a minimum full-flow rate (for hydrogen release) of 0.02 (g/s)/kW is typically required for proper fuel-cell operation. During the hydrogen recharging, a significant amount of heat has to be extracted, while the appropriate amount of heat has to be supplied to generate proper hydrogen desorption rate. Thus, efficient cooling/heating of the storage device to match the optimum operating temperature (along with facile inherent material kinetics) of a given storage material is essential to meet these requirements. This drives the need to characterize the engineering properties (such as, for example, capacity, kinetics, thermo-conductivity, cyclability, impurity effects, etc.) of various candidate hydrogen storage materials, particularly in combination with various associated heat exchanging structures.

Interfacial heat resistance and thermal conductivity may be important engineering properties to characterize for any devices in which heat generation and transfer tend to limit the rate of the concerned processes, such as the rates of hydrogen absorption and desorption for a given hydrogen storage material. Conventional thermal characterization techniques complying with ASTM D-5470-06 typically employ a pressure vessel containing a single storage material, and a heat exchanger (including fins and coolant tubes) running through the sample material. In such systems, the heat resistances from three interfaces (materials-heat exchanger, materials-vessel, and materials-coolant tube) are typically measured. Operating this type of test system presents certain challenges. First, heat-resistance data for the material and heat exchanger is confounded with data from the material-vessel and material-coolant interfaces. Thus in order to isolate the thermal information for the desired material-heat exchanger interface, one may need to perform tedious calibration and data processing in order to subtract out the effects of the other two interfaces. Second, the structure of such pressure vessel test setups typically allows only one storage material and heat exchanger combination to be measured at a time. Third, the measurement process used with such systems tends to be costly and challenging due to the large amount of sample material required to fill the vessel and the time-consuming manner in which the sample is typically loaded and packaged.

SUMMARY

In certain examples, a hydrogen storage engineering properties analyzer may comprise a cover, a sample tray and a base. A sample tray typically includes an array of cooling fins, each cooling fin having a respective sample well formed within the cooling fin. Each sample well may include a sample well opening through which a hydrogen storage material can be loaded into and removed from the respective sample well. The sample tray and cover may be combinable to define a plenum in fluid communication between the sample well openings and the fluid port.

The base may include a surface defining a cooling chamber configured to receive the cooling fins. The base may have a flange portion configured to receive a plurality of fastener elements by which the base, the sample tray and the cover can be secured together in sealed fashion. Embodiments typically include a coolant inlet and a coolant outlet, each being in fluid communication with the cooling chamber. In particular embodiments, the coolant inlet and outlet may be disposed on opposing sides of the base.

Certain embodiments may include a cover seal element and a base seal element. The cover seal element may be configured to ensure a seal between the cover and the sample tray so as to prevent fluid leakage from the plenum. The base seal may be configured to ensure a seal between the base and the sample tray so as to prevent coolant leakage from the cooling chamber.

Particular embodiments may include a pressure transducer in fluid communication with the fluid port. Further embodiments may include one or more thermal transducers attached to one or more of the cooling fins, for example, within the sample well, on the outside surface of the cooling fin, or both.

Embodiments may be characterized as "high-throughput" hydrogen storage engineering properties analyzers because they may be used to simultaneously evaluate many different storage material and heat exchanger combinations. Embodiments may also enable the rapid cooling or heating of a significantly large quantity of hydrogen storage material, and provide for quantitative measurement of heat transfer, thermal properties, hydrogen capacity, and kinetics under a variety of operating temperature-pressure conditions.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

The kinetic rates of a hydrogen storage system define the refueling rate (hydrogen uptake) and supply rate of fuel (hydrogen release) to a fuel cell. These kinetic rates are determined by a number of factors including the intrinsic kinetic properties of the storage material. At the system level, several characteristics contribute to the kinetic rate, including heat transfer between the storage material, material housing (including heat exchanger) and environment, the operating over- or under-pressure relative to the materials thermodynamic equilibrium pressure, and the packing density of the storage material. Most materials rely on the effective supply and dissipation of significant amounts of energy (as heat) during charging and discharging. Thus, heat transfer may play a crucial role in the ultimate kinetic performance of a materials-based hydrogen storage system. As an example, rehydriding 5 kg of hydrogen within 3 minutes for a material that possesses a reaction enthalpy ($\Delta H$) of 20 kJ/mol.$H_2$ requires almost 300 kW of cooling load. As an additional example, most sorbent materials such as metal-organic frameworks (MOFs) currently operate at cryogenic temperatures. Therefore, the corresponding containment device for a sorbent should be capable of cooling the material down to 77 K in less than the desired three minute refueling time. Overall, the ability to handle significant energy loads (e.g., for cooling, heating, or heat dissipation) requires effective and often-complicated thermal management systems.

With regard to the several figures shown herein, certain embodiments of a hydrogen storage engineering properties analyzer are shown generally at 100. Certain embodiments may be capable of rapidly and simultaneously evaluating the heat transfer properties of various hydrogen storage media 118 in association with selected heat exchanging materials. The intrinsic interfacial heat transfer properties between hydrogen storage materials and the heat exchangers can be accurately determined and are not confounded with the ancillary interfaces that exist in typical state-of-the-art analyzers. Embodiments may at times be characterized as "high-throughput" because they make possible the simultaneous collection of thermal data and evaluation of overall storage properties of a wide variety of hydrogen storage materials, including conventional metal hydrides, complex hydrides, sorbents, and chemical hydrides for a given heat exchanging material. The identity of the heat exchanging materials is also variable.

Figure 1:
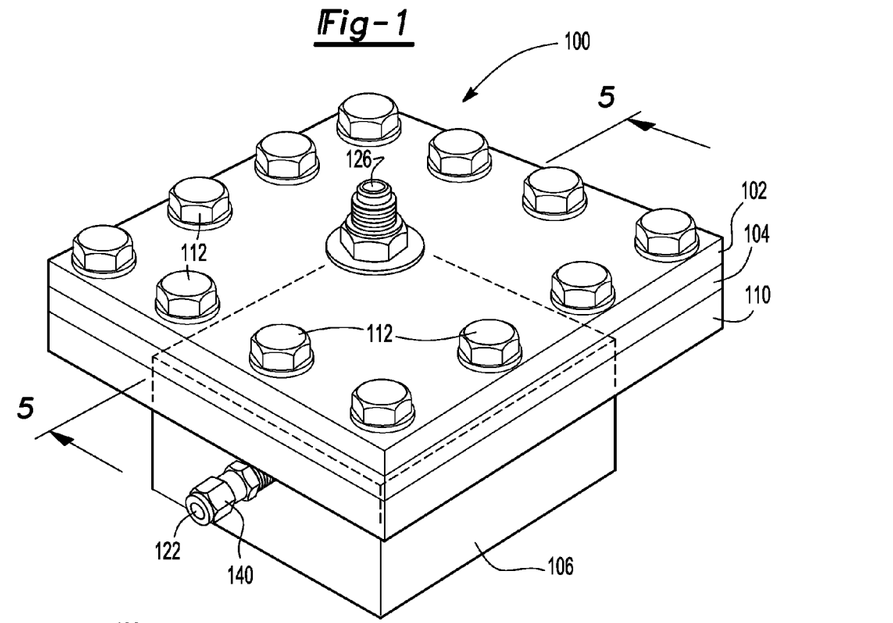
FIG. 1 is a diagrammatic perspective view of an embodiment of a hydrogen storage engineering properties analyzer.
Figure 2:
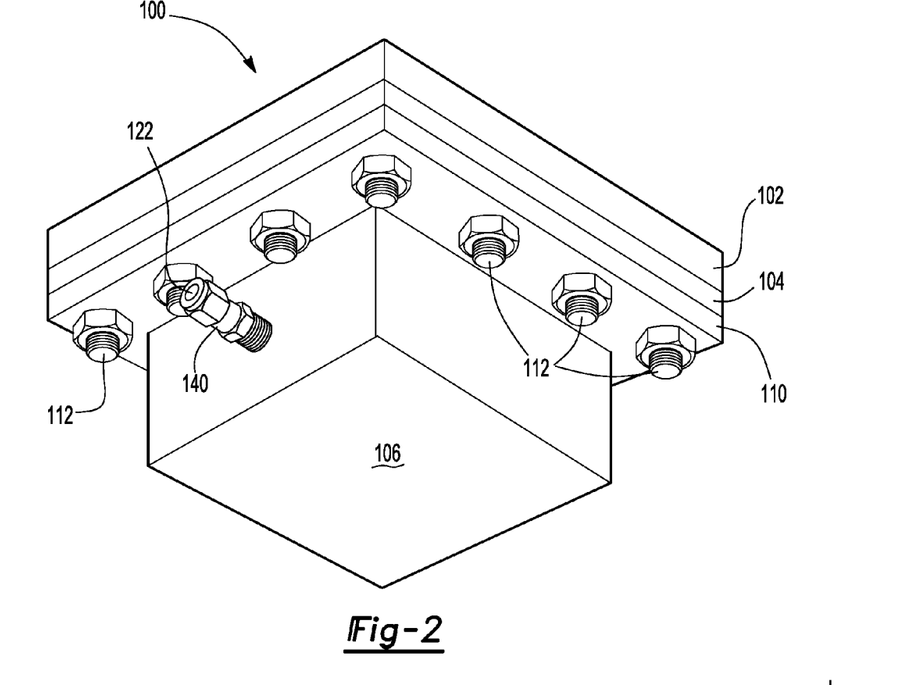
FIG. 2 is a further diagrammatic perspective view of the embodiment shown in FIG. 1.
Figure 3:
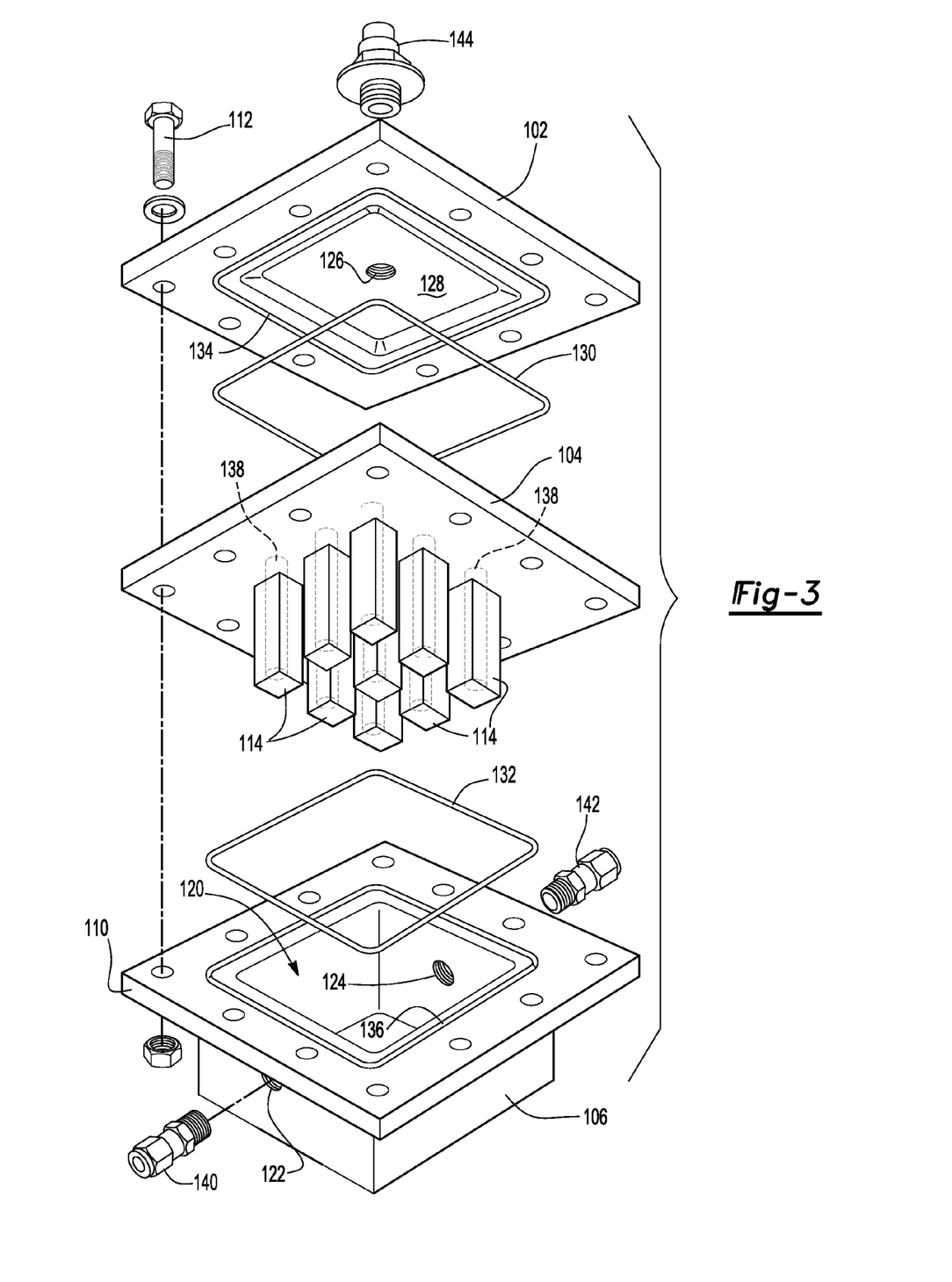
FIG. 3 is a diagrammatic exploded view of the embodiment shown in FIG. 1.
Figure 4:
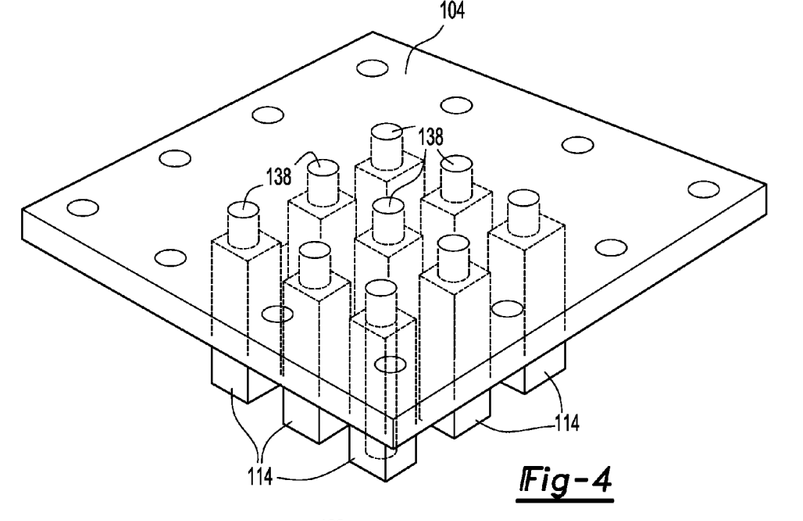
FIG. 4 is a diagrammatic perspective view of a sample tray of the embodiment shown in FIG. 1.
Figure 5:
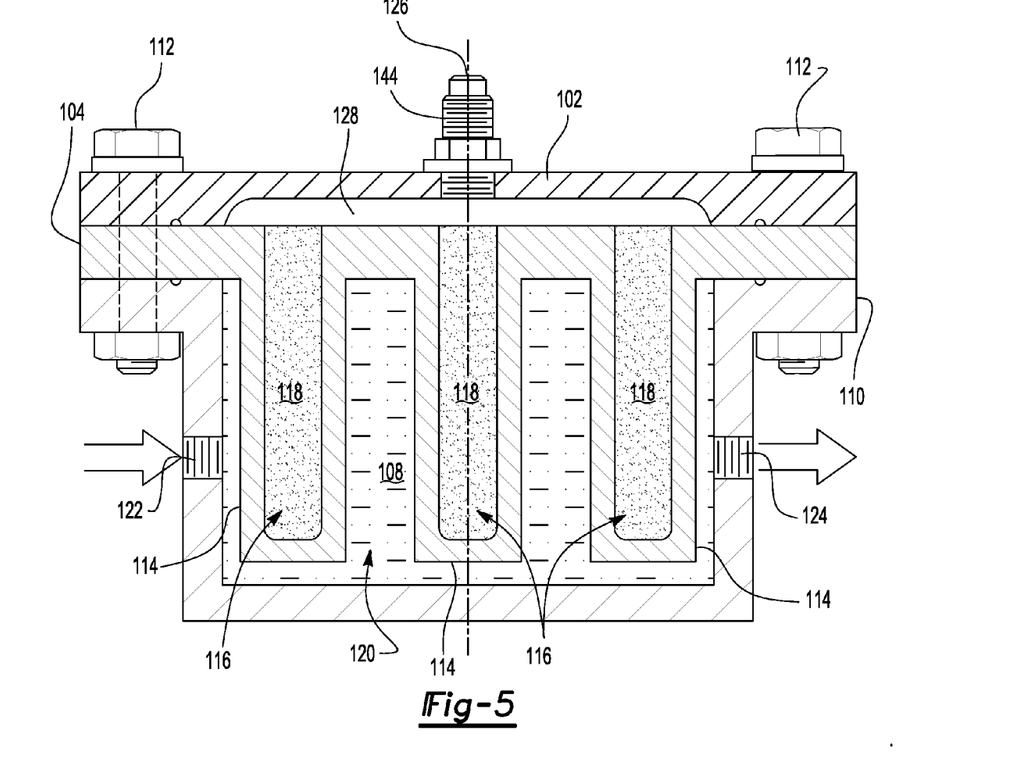
FIG. 5 is a diagrammatic cross-sectional view taken along line 5-5 of FIG. 1.

Referring to FIGS. 3 and 5 for illustration, embodiments of the storage properties analyzer 100 may generally include a cover 102, a sample tray 104, and a base 106. By minimizing the number of components, the required sealing surfaces are minimized as well, thereby helping to avoid potential leaks of, for example, either hydrogen gas or liquid coolant 108 from the analyzer 100 during its operation. The combination of the cover 102 and sample tray 104 may be referred to herein as the storage vessel.

In certain preferred embodiments, the base 106 may include a flange portion 110 configured to receive fastener elements 112, such as bolts, clamps or the like, to releasably fasten the base 106, sample tray 104 and cover 102 together.

In embodiments, a sample tray 104 typically includes a plurality of hollow posts or cooling fins 114. Each cooling fin 114 may contain a sample well 116 that is capable of holding a sample of hydrogen storage material 118, such as, for example, cryogenic sorbent (e.g., MOF). In addition to sample containment, these separate sample posts serve as heat exchanging fins that facilitate rapid cooling of the storage material 118. The sample tray 104 is configured to sit inside a bath or cooling chamber 120 through which a continuous flow of coolant 108, for example, liquid nitrogen, may be pumped. A coolant inlet 122 and a coolant outlet 124 may be located, for example, on opposite sides of the base 106 to provide the coolant flow between the cooling fins 114 of the sample tray 104 at a controlled flow rate. In certain preferred embodiments, the coolant reservoir within the coolant chamber 120 can operate, for example, anywhere from 77 to 673 K at a flow rate from 0 to 2 L/m utilizing diverse heating or cooling liquids.

In embodiments, the sample tray 104 also typically serves as the heat exchanger, thereby avoiding the introduction of separate materials which would confound the thermal property data. The sample tray 104 can be constructed from a variety of materials of interest, including, for example, Aluminum, steels, other appropriate or conventional heat-exchanger materials, or the like. The sample wells 116 within the cooling fins 114 of the sample tray 104 are distributed apart so they can be loaded with different hydrogen storage materials by way of respective well openings 138. The sample tray 104 and cover 102 may define a plenum 128, which is typically in fluid communication between the sample well openings 138 and the fluid port 126. Once the sample wells 116 are filled with respective storage materials 118, all of the engineering properties can be collected simultaneously for all the sample storage materials 118 in association with a selected sample tray 104 material.

The cover 102, which may be configured to be fastened to the top of the sample tray 104 for sealing, may include a fluid port 126 for either evacuating or pressurizing the sample material 118 by way of the plenum 128. Certain embodiments may include more than one fluid port 126. For example, one of the fluid ports 126 may be dedicated to introducing pressurized hydrogen gas to the plenum 128, and another may be dedicated to evacuation of the plenum 128. A further fluid port 126 may be included for the purpose of introducing a secondary gas to the plenum 128. In certain embodiments having only one fluid port 126, the plenum 128 may be both pressurized and evacuated by way of that fluid port.

As illustrated, for example, in FIG. 3, a fluid port 126, a coolant inlet 122, coolant outlet 124 may each be associated with a respective fitting. For example, the inlet fitting 140 and outlet fitting 142 may be adapted to quickly connect the coolant chamber 120 into a coolant circuit. Similarly, fluid port fitting 144 may be adapted to facilitate the rapid connection of the plenum 128 to, for example, a controlled source of pressurized hydrogen gas.

Referring to FIG. 3 for illustration, with respect to particular illustrated embodiments, grooves 134 and 136 for a sealing material are shown on the cover 102 and base 106, respectively. Relatedly, certain embodiments may include, for example, a cover seal element 130 and a base seal element 132. The seal elements may be made of a variety of materials appropriate for use in pressurized systems. For example, while indium metal seals have been shown to work effectively in cryogenic, high pressure conditions, less expensive alternatives may be used, such as graphite seals.

Embodiments typically include one or more pressure sensors and thermal sensors (not shown) for control and data collection. Certain embodiments include, for example, at least one pressure transducer in fluid communication with each fluid port 126. Thermal transducers, such as thermocouples, may be disposed, for example, within one or more of the sample wells 116 or on the outside of the cooling fins 114. In certain embodiments, for example, thermocouples may be placed toward the closed end of the sample wells 116 and on the outer surface of each respective cooling fin 114. They may be affixed to the respective cooling fin 114 or sample well 116 by way of, for example, epoxy or other appropriate adhering or fastening means. Wiring from the thermal sensors may exit the analyzer assembly 100, by way of, for example, one or more sealed wiring conduit ports or the like. By way of example, wiring from the thermal transducers within various sample wells 116 may exit a single sealed wiring harness in the cover 102. The pressure transducers and thermal transducers are generally connected to appropriate electronic hardware to facilitate data acquisition and automatic control.

In typical embodiments, the cover 102, sample tray 104 and base 106 are made of the same material so as to avoid breaching of the joint seals, which may otherwise result from disparate thermal expansion and contraction under operating conditions. For example, in particular embodiments, the cover 102, sample tray 104 and base 106 may be formed of aluminum 6061, which has been shown to provide good structural properties through a high yield stress, while retaining a significant advantage in thermal transfer coefficient as compared with steel alloys. Thus, embodiments can remain relatively compact while maintaining their functionality, for example supporting high pressure recharge and rapid temperature response.

It is envisioned that in certain embodiments, the combination of the cover 102 and sample tray 104 may define two or more separate plenums 128, wherein, for example, one plenum is in fluid communication with one set of sample wells, and another plenum is in fluid communication with another set of sample wells. In such embodiments, the cover 102 and sample tray 104 may still preferably each be formed from a single piece of material. Such embodiments may also feature, for example, a separate cover seal element 130 disposed around each plenum 128.

Figures 6, 7, 8:
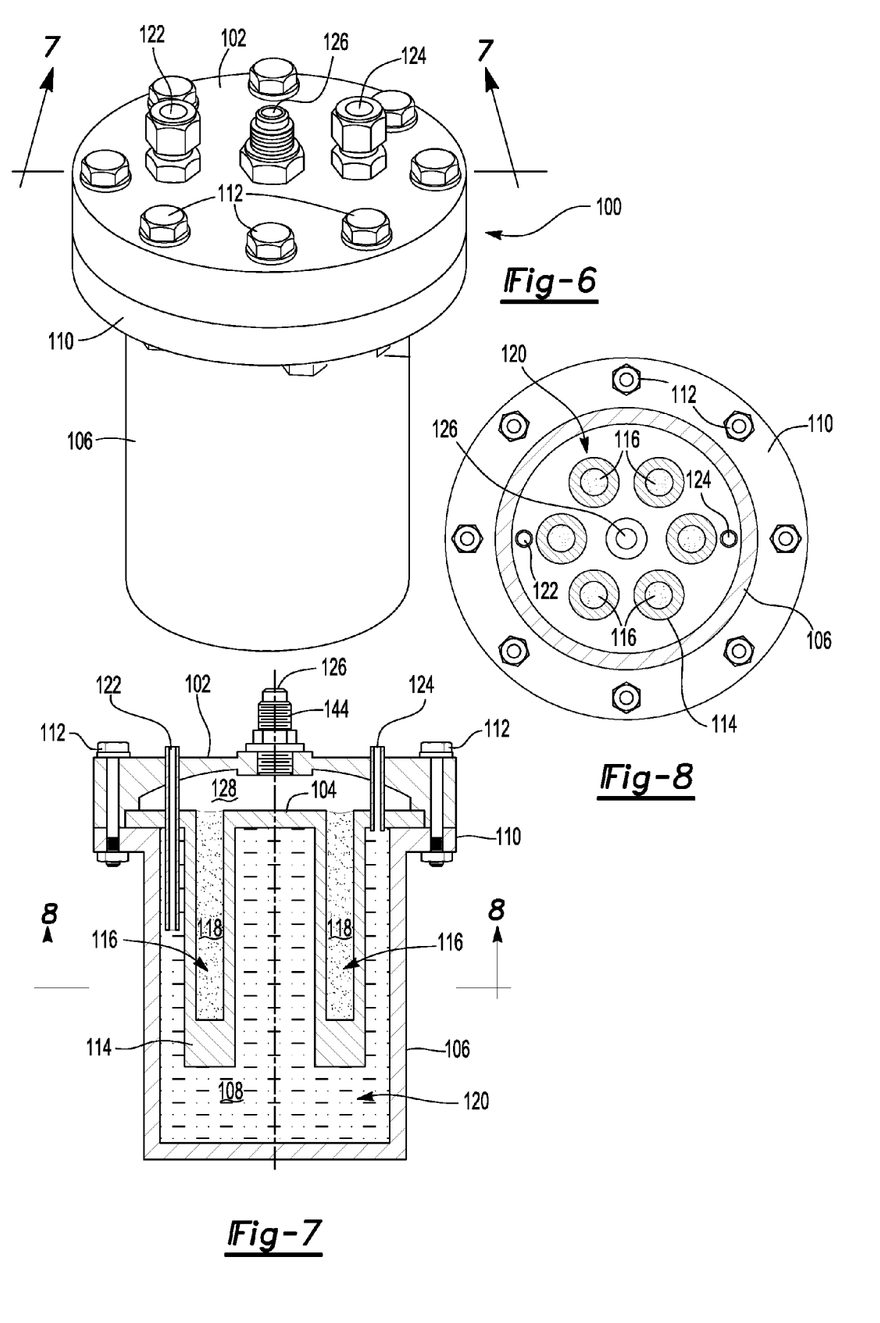
FIG. 6 is a diagrammatic perspective view of a further embodiment of a hydrogen storage engineering properties analyzer.
FIG. 7 is a diagrammatic cross-sectional view taken along line 7-7 of FIG. 6.
FIG. 8 is a diagrammatic cross-sectional view taken along line 8-8 of FIG. 7.

In particular embodiments, such as the one illustrated in FIGS. 6-8, the coolant inlet 122 and coolant outlet 124 may extend through the cover 102 and sample tray 104 such that neither the coolant inlet 122 or coolant outlet 124 are in fluid communication with the plenum 128.

The ultimate dimensions and capacity of various embodiments of an analyzer 100 can be selected based on the desired storage material composition or application. By way of example, in a preferred embodiment the sample wells 116 have been formed with a volume of 5000 mm³, making them particularly appropriate to house a cryogenic metal-organic framework (MOF). Such an embodiment may aim to store, for example, 5-10 g of hydrogen in MOF-177.

Figure 9:
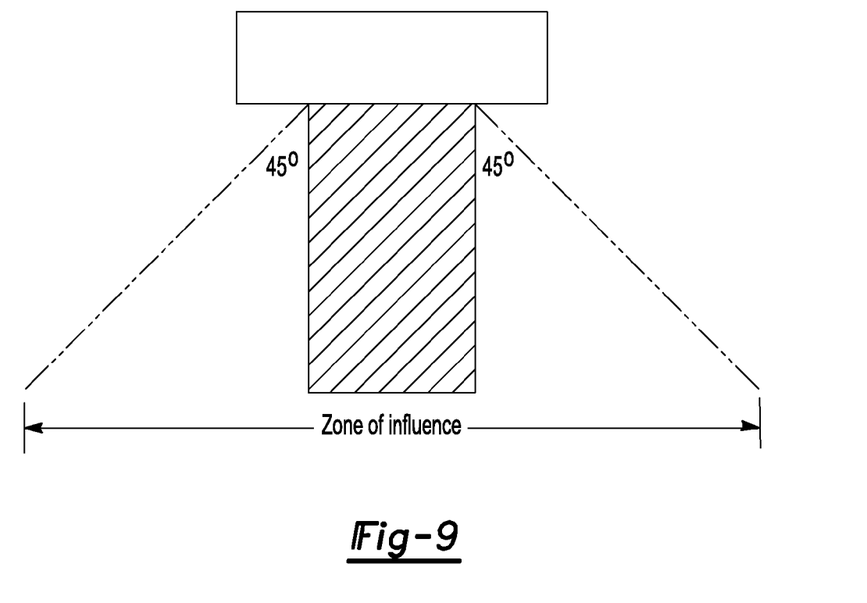
FIG. 9 diagrammatically illustrates the zone of influence of a tightened bolt.

As illustrated throughout the several figures, a through-hole bolt pattern has been designed to provide the clamping force needed for sealing. The bolt hole spacing was determined by using the zone of influence created by a tightened bolt, which encompasses the conical region emanating at a 45° angle from where the bolt shoulder meets the head. The bolts 112 are spaced such that there is a small overlap between the zones of influence of the bolts at the highest sealing surface. FIG. 9 illustrates the zone of influence of a tightened bolt.

As illustrated, for example, in FIG. 5, in at least one preferred embodiment, the pressure chamber, which includes the plenum and sample wells, is generally devoid of sharp inside corners in order to avoid introducing unnecessarily high stress concentrations when the pressure chamber operates at, for example, 100 bar of internal pressure. The sample wells 116 are typically cylindrical with filleted bottom geometry for the same reason. The wall thickness for the posts or fins 114 in this exemplary embodiment was chosen based on the stress tensor equations for a cylindrical pressure vessel:

$$\sigma_1 = (pb^2)/(a^2-b^2) \quad \text{(Eq 1)}$$

$$\sigma_2 = [(pb^2)*(a^2+r^2)]/[r^2*(a^2-b^2)] \quad \text{(Eq 2)}$$

$$\sigma_3 = [-(pb^2)*(a^2-r^2)]/[r^2*(a^2-b^2)] \quad \text{(Eq 3)}$$

$$\tau_{2,3} = (\sigma_2 - \sigma_3)/2 \quad \text{(Eq 4)},$$

where $\sigma_1$ is the stress tensor in cylindrical coordinates with 1 corresponding to the z direction depth, 2 is along the theta direction circumference, and 3 is along the radial thickness, $\tau$ is the shear stress, with the 2,3 direction being the only non-zero shear component, p is the internal pressure of the vessel, a and b are the outer and inner radii of the vessel, respectively, and r is the radial distance throughout the wall thickness. The maximum values of each component of the stress tensor occur when r=b at the inner wall of the vessel:

$$\sigma_{1,max} = (pb^2)/(a^2-b^2) \quad \text{(Eq 5)}$$

$$\sigma_{2,max} = p*(a^2+b^2)/(a^2-b^2) \quad \text{(Eq 6)}$$

$$\sigma_{3,max} = -p \quad \text{(Eq 7)}$$

$$\tau_{2,3,max} = p*a^2/(a^2-b^2) \quad \text{(Eq. 8)}.$$

The yield condition of such a pressure vessel can be approximated by the Von Mises yield stress $\sigma_y$:

$$\sigma_y = (\tfrac{1}{2}*[(\sigma_1-\sigma_2)^2 + (\sigma_2-\sigma_3)^2(\sigma_3-\sigma_1)^2] + 3\tau)^{1/2} \quad \text{(Eq. 9)}.$$

Figure 10:
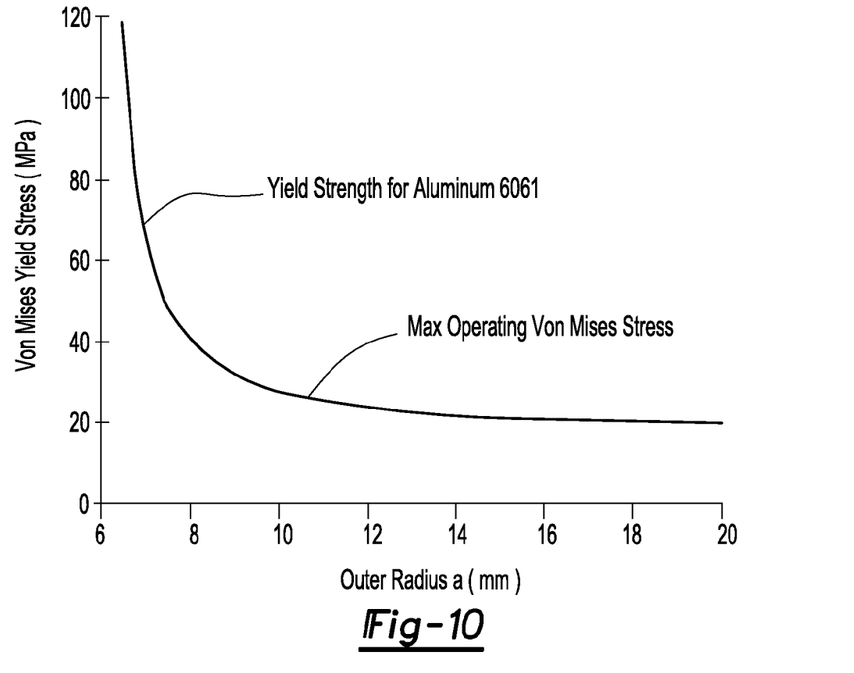
FIG. 10 is a plot illustrating the Von Mises yield condition versus outer radius a, with a fixed inner radius b=6 mm.

Plastic deformation begins to occur when the Von Mises yield stress exceeds the material yield stress. The vessel is designed such that an internal pressure of 100 bar does not cause plastic deformation with an added factor of safety. The curve showing the Von Mises yield stress versus varying outer radius a with a fixed inner radius b=6 mm is shown in FIG. 10.

In at least one preferred embodiment, the inner radius of the sample wells 116 was determined by the requirement to store 15 g of hydrogen in the vessel and is based on the MOF material properties. The material yield stress of aluminum 6061 is 55.2 MPa. This yield strength is accurate from room temperature down to the cryogenic temperatures for which the device is designed to operate. In the embodiment, the minimum wall thickness between the wells 116 and outer dimension of the fins 114 of the sample tray 104 was designed to be 4 mm and is the location of the failure mode for the particular embodiment. This corresponds to a minimum outer radius of 10 mm and a Von Mises stress of less than 30 MPa, as shown, for example, in FIG. 10. This leaves nearly a factor of safety of 2 to account for imperfections in the tray material, subtle yield strength variations due to temperature, and spikes in pressure during operation.

Various aspects of embodiments of the analyzer 100 are typically alterable to allow further evaluation of engineering properties. For example, the components of the device could be manufactured of different materials with varying yield strength and thermal transfer coefficient values, depending on future requirements and performance targets. Different coolant strategies could be employed to further refine the cooling efficiency. Fin design is easily altered in number, configuration, and shape to improve cooling or provide more efficient hydrogen sorption. For example, cooling fins may be arranged in a rectangular array (see, for example, FIG. 3), a circular array (see, for example, FIG. 8), or another preferred arrangement. Further, the balance between fin size, coolant spacing between fins, construction material, and wall thickness may all be optimized to control volumetric and gravimetric densities at the system level. Ultimately, individual embodiments can be customized to accommodate a desired attribute such as hydrogen storage properties, or to balance characteristics including desired weight, cost, and size of the analyzer. In particular embodiments, the sandwich style design of the module helps eliminate or minimize possible thermal expansion issues which may otherwise arise if, for example, the sample tray 104 were to be constructed of a material which differs from the cover 102 and the base 106.

Embodiments may be equally capable of use in performing experiments with any current hydrogen storage material, or any material that requires both a pressure chamber and rapid temperature change. As discussed herein, certain preferred embodiments have been specifically designed to work with hydrogen storage materials such as MOF (metal-organic frameworks) and both chemical and complex hydrides. The ability to use the heat exchanger for both cooling and heating purposes allows further versatility in material testing.

Embodiments may be easily scaled up to simulate the vehicle operating requirements for a vehicle level system in terms of the amount of hydrogen carried on board to achieve full vehicle range. Embodiments may also be considered modular in the sense that several units could be run either in parallel or series to improve total hydrogen storage capacity or test efficiency. For example, certain embodiments may be modularly interconnectable so as to allow, for example, a plurality of such analyzers 100 to share the same liquid coolant circuit or hydrogen source.

Embodiments of an analyzer 100 may provide numerous advantages over conventional test set-ups. For example, embodiments are anticipated to improve efficiency in testing time, materials and overall cost, particularly when compared to most state-of-the-art hydrogen properties analysis methods which typically involve "one-at-a-time" construction of pressure vessels and heat exchanger tubes. Such conventional systems often produce poor data resolution with respect to thermal properties and require large amounts of costly research materials. Contrastingly, embodiments as discussed, for example, may enable high-throughput materials-based hydrogen storage system design and validation through rapid screening and optimization of hydrogen storage media and ancillary component materials (e.g., heat exchanger and vessel). In particular, embodiments provide an efficient means for characterizing heat transfer properties between candidate coolants, candidate heat exchangers and candidate hydrogen storage media as a function of hydrogen absorption and desorption conditions (hydrogen A/D pressure and temperature, coolant temperature and flow rate). In addition to the automotive market, embodiments are envisioned to prove useful to consumer products manufacturers, auto parts suppliers, pharmaceutical industries, and medical instrument developers, some of which require similar screening methods.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A hydrogen storage engineering properties analyzer comprising:
    a cover including a fluid port;
    a pressure transducer in fluid communication with the fluid port;
    a sample tray including a plurality of cooling fins, each of the cooling fins including a sample well formed therein, the sample wells being distributed apart from each other such that different hydrogen storage materials may be loaded therein by way of respective sample well openings, at least one of the sample wells including a thermal transducer, the sample tray and the cover defining a plenum in fluid communication between the sample well openings and the fluid port;
    a base including a surface defining a cooling chamber configured to receive the cooling fins, the base having a flange portion configured to receive a plurality of fastener elements for fastening the base, the sample tray and the cover together;
    a coolant inlet and a coolant outlet extending through the cover and sample tray such that neither the coolant inlet or coolant outlet are in fluid communication with the plenum, each being in fluid communication with the cooling chamber and disposed on opposing sides of the base; and
    a cover seal element and a base seal element, the cover seal element being sealingly disposed between the cover and the sample tray so as to prevent fluid leakage from the plenum, the base seal being sealingly disposed between the base and the sample tray so as to prevent coolant leakage from the cooling chamber.

2. A hydrogen storage engineering properties analyzer as defined in claim 1 further comprising a liquid coolant within the cooling chamber and a plurality of hydrogen storage materials, at least two of the hydrogen storage materials being different from each other, each of the hydrogen storage materials being disposed within a respective one of the sample wells.

3. A hydrogen storage engineering properties analyzer as defined in claim 1 wherein the cover, the sample tray and the base are made of substantially the same material.

4. A hydrogen storage engineering properties analyzer as defined in claim 2 wherein at least one of the hydrogen storage materials is a cryogenic metal-organic framework.

5. A hydrogen storage engineering properties analyzer comprising:
    a cover including a fluid port;
    a sample tray including a plurality of cooling fins, each of the cooling fins including a sample well formed therein, the sample wells being distributed apart from each other such that different hydrogen storage materials may be loaded therein by way of respective sample well openings, the sample tray and the cover defining a plenum in fluid communication between the sample well openings and the fluid port;
    a base including a surface defining a cooling chamber configured to receive the cooling fins, the base having a flange portion configured to receive a plurality of fastener elements for fastening the base, the sample tray and the cover together;

a coolant inlet and a coolant outlet extending through the cover and sample tray such that neither the coolant inlet or coolant outlet are in fluid communication with the plenum, and each being in fluid communication with the cooling chamber; and a hydrogen storage material within one or more of the sample wells, and a liquid coolant within the cooling chamber.

6. A hydrogen storage engineering properties analyzer as defined in claim 5 wherein the cover, the sample tray and the base are made substantially of 6061 aluminum.

7. An analyzer comprising:

a cover;

a sample tray including a plurality of distributed cooling fins each including a sample well formed therein, the sample tray and cover defining a plenum in fluid communication with the sample wells;

an inlet and outlet extending through the cover and sample tray such that neither the inlet or outlet are in fluid communication with the plenum; and a base defining a cooling chamber configured to receive the cooling fins.

8. An analyzer as defined in claim 7 further comprising a cover seal element and a base seal element, the cover seal element being configured to be sealingly disposed between the cover and the sample tray, the base seal element being configured to be sealing disposed between the base and the sample tray.

9. An analyzer as defined in claim 7 wherein the cooling fins are distributed in a rectangular array.

10. An analyzer as defined in claim 7 wherein the cooling fins are distributed in a circular array.

11. An analyzer as defined in claim 7 wherein the cooling fins have a cross-sectional shape which is substantially rectangular.

12. An analyzer as defined in claim 7 further comprising a fluid port extending through the cover and in fluid communication with the plenum.

13. An analyzer as defined in claim 7 wherein the base includes a flange portion configured to receive a plurality of fastener elements for fastening the base, the sample tray and the cover together.

14. An analyzer as defined in claim 7 wherein the cover, the sample tray and the base are made of substantially the same material.

15. An analyzer as defined in claim 7, further comprising a plurality of fluid ports, each of the fluid ports being in fluid communication with the plenum.

16. An analyzer as defined in claim 7, further comprising hydrogen storage material within one or more of the sample wells, and liquid coolant within the cooling chamber.

* * * * *